United States Patent [19]

Küng et al.

[11] Patent Number: 5,424,317
[45] Date of Patent: Jun. 13, 1995

[54] FUNGICIDAL COMPOSITIONS

[75] Inventors: Ruth Küng, Dielsdorf, Switzerland; Dominique G. G. Driant, Paris, France

[73] Assignee: Ciba-Geigy Corporation, Ardsley, N.Y.

[21] Appl. No.: 230,666

[22] Filed: Apr. 21, 1994

Related U.S. Application Data

[60] Division of Ser. No. 993,510, Dec. 18, 1992, Pat. No. 5,330,984, which is a continuation of Ser. No. 883,908, May 13, 1992, abandoned, which is a continuation of Ser. No. 784,199, Oct. 28, 1991, abandoned.

[30] Foreign Application Priority Data

Nov. 2, 1990 [CH] Switzerland ............... 3491/90

[51] Int. Cl.⁶ ............... A01N 43/40; A01N 43/64
[52] U.S. Cl. ............... 514/317; 514/383
[58] Field of Search ............... 514/383, 317

[56] References Cited

U.S. PATENT DOCUMENTS

| | | |
|---|---|---|
| 4,241,058 | 12/1980 | Pfiffner ............... 424/248 |
| 4,814,331 | 3/1989 | Kerkenaar ............... 514/231.5 |
| 4,925,842 | 5/1990 | Janicke et al. ............... 514/239.5 |
| 5,229,397 | 7/1993 | Seele et al. ............... 514/317 |

FOREIGN PATENT DOCUMENTS 0251775  1/1988  European Pat. Off. .
0453922  10/1991  European Pat. Off. .

OTHER PUBLICATIONS

Driant et al, C.A., vol. 110, (1989) 110;130;378e.
Pesticide Manual, 9th Ed. p. 157, which relates to Component I (1985).
Worthing et al., The Pesticide Manual, 8th Ed. p. 383 (1987).
Charles R. Worthing, The Pesticide Manual, Seventh Edition (1983) p. 265.

*Primary Examiner*—Allen J. Robinson
*Attorney, Agent, or Firm*—Edward McC. Roberts

[57] ABSTRACT

Plant fungicidal compositions based on two active ingredients a) and b) show a synergistically increased effect in the case where component a) is 4-(4-chlorophenyl)-2-phenyl-2[(1H-1,2,4-triazol-1-yl)methyl]butane nitrile and component b) is either fenpropimorph or fenpropidin or a mixture of the two.

4 Claims, No Drawings

FUNGICIDAL COMPOSITIONS

This is a division of Ser. No. 07/993,510, filed Dec. 18, 1992, now U.S. Pat. No. 5,330,984, continuation of Ser. No. 07/883,908, filed May 13, 1992, now abandoned, which is a continuation of Ser. No. 07/784,199, filed Oct. 28, 1991, now abandoned.

The present invention relates to novel active substance combinations for controlling plant diseases and to processes for applying such mixtures for leaf, soil and seed dressing application.

The combinations according to the invention comprise a) 4-(4-chlorophenyl)-2-phenyl-2-[(1H-1,2,4-triazol-1-yl)methyl]butane nitrile of the formula I

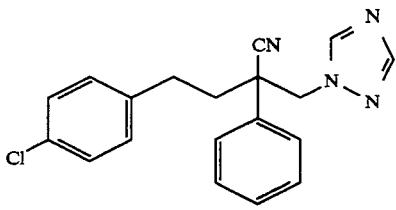

or acid addition salts and metal complexes thereof, and b) cis-4-[3-(4-tert-butylphenyl)-2-methylpropyl]-2,6-dimethylmorpholine of the formula II

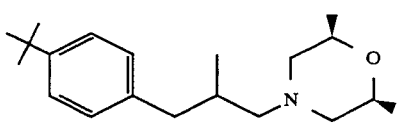

or acid addition salts thereof and/or 1-[3-(4-tert-butylphenyl)-2-methylpropyl]piperidine of the formula III

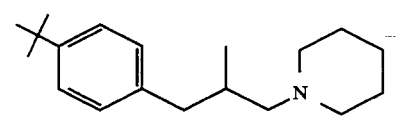

or acid addition salts thereof.

Component a) has become known under the code designation RH-7592. Its synthesis and fungicidal properties are described in EP 0 251 775.

Component b) has become known under the name fenpropimorph and component c) under the name fenpropidin. Their syntheses and fungicidal properties are described in German Offenlegungsschrift 2 752 135.

Surprisingly, it was found that the fungicidal action of the active ingredient (a.i.) combination according to the invention is significantly higher than the sum of the actions of the individual active substances. This means that an unforeseeable synergistically increased action is present and not only an additive action as could have been expected by the combination of two active substances. The active substance combinations according to the invention thus constitute an enlargement of the art.

When the active substances are present in the active substance combinations (hereafter called the mixtures) according to the invention in specified weight ratios, the synergistic effect is particularly apparent However, the weight ratios of the active substances in the active substance combinations can be varied within a relatively wide range, depending on the type of application. In general, 0.2–20 pans by weight, preferably 0.5–10 pans by weight of active substance(s) of the formula (II) and/or (III) are present per pan by weight of active substance of the formula (I). This corresponds to a weight ratio of component a) to component b) of 5:1 to 1:20. Particular preference is given to combinations in which 1 to 8 pans by weight of active substance(s) of the formula (II) and/or (III) are present per part by weight of the formula (I), in particular a):b)=2:1 to 1:10 and very particularly 1:1 to 1:4. Examples of mixing ratios of a):b) which are particularly suitable for practical application are 2:3; 2:5; 1:2 and 1:3. The above weight ratios apply regardless of whether the active components' acid addition salts or metal complexes are used.

Examples of acids which can be used for preparing salts of the formula I, II or Ill are: hydrohalic acids such as hydrobromic acid and hydrochloric acid, furthermore phosphoric acid, nitric acid and sulfuric acid, furthermore mono-, hi- or trifunctional carboxylic acids and hydroxycarboxylic acids such as formic acid, succinic acid, acetic acid, glycolic acid, fumaric acid, lactic acid, oxalic acid, propionic acid, sorbic acid, trichloroacetic acid, trifluoroacetic acid, citric acid, furthermore sulfonic acids such as benzenesulfonic acid, 1,5-naphthalenedisulfonic acid and p-toluenesulfonic acid and (thio)saccharin.

Metal complexes consist of the basic organic molecule and an inorganic or organic metal salt, for example halides, nitrates, sulfates, phosphates, acetates, trifluoroacetates, trichloroacetates, propionates, tartrates, sulfonates, salicylates, benzoates, and the like, of the elements of main group III or IV, such as aluminium, tin or lead and of subgroup I to VIII, such as chromium, manganese, iron, cobalt, nickel, copper, zinc, and the like. Preference is given to subgroup elements from the 4th period. In these metal complexes, the metals can be present in the various valencies in which they usually occur.

The active substance mixtures according to the invention and acid addition salts thereof have plant fungicidal action and can therefore be used for controlling fungi in agriculture and horticulture. They are suitable in particular for inhibiting the growth of or for destroying phytopathogenic fungi on parts of plants, for example leaves, stalks, roots, tubers, fruits or flowers, and on seeds and of harmful fungi present in the soil.

The active substance mixtures according to the invention are suitable in particular for controlling ascomycetes (*Erysiphe graminis, Uncinula necator*, Venturia, *Sphaerotheca pannosa, Erysiphe betae*) and basidiomycetes, which include rusts, for example those of the genera Puccinia, Uromyces and Hemileia (in particular *Puccinia recondita, Puccinia striiformis, Puccinia graminis, Puccinia coronata, Uromyces fabae, Uromyces appendiculatus, Hemileia vastatrix*). Furthermore, the active substance combinations according to the invention act against Fungi imperfecti of the genera Helminthosporium (for example *Helminthosporium oryzae, Helminthosporium teres, Helminthosporium sativum, Helminthosporium tritici-repentis*), Alternaria (for example *Alternaria brassicola, Alternaria brassicae*), Septoria (for example *Septoria avenae*), Cercospora (for example *Cercospora beticola*), Ceratocystis (for example *Ceratocystis*

*ulmi*), Pyricularia (for example *Pyricularia oryzae* and *Mycospharella fijiensis*).

The active substance combinations according to the invention are suitable in particular also for controlling mould strains which have developed a certain resistance towards active substances from the class of triazoles.

In the field, it is preferred to use dosages of 75 to 1000 g of active substance mixture per hectare and treatment. For controlling fungi in dressing treatments of seeds, dosages of 0.01 g to 1.0 g of active substance mixture are advantageously used per kg of seed.

Analogously, these data also apply to plant propagation material in general, i.e. also for kg amounts of cuttings, tubers, root material, and the like.

The fungicide combinations according to the invention are distinguished by systemic, curative and preventive action.

The active substance mixtures according to the invention can be formulated to give a wide range of agents, for example solutions, suspensions, emulsions, emulsifiable concentrates and pulverulent preparations. The present invention also relates to the fungicidal compositions of this type. The fungicidal compositions according to the invention comprise an effective amount of RH-7592 and fenpropimorph and/or fenpropidin or acid addition salts or metal complexes of these active substances and formulation agents. Advantageously, the compositions contain at least one of the following formulation agents: solid carriers; solvents or dispersants; surfactants (wetting agents and emulsifiers); dispersants (without surfactant action); and additives of other types, such as stabilisers.

Suitable solid carriers are in particular: natural minerals, such as kaolin, clays, kieselguhr, talc, bentonite, chalk, for example whiting, magnesium carbonate, limestone, quartz, dolomite, attapulgite, montmorillonite and diatomaceous earth; synthetic minerals, such as highly disperse silica, alumina and silicates; organic materials, such as cellulose, starch, urea and synthetic resin; and fertilisers, such as phosphates and nitrates, it being possible for carriers of this type to be present, for example, as granules or powders.

Suitable solvents or dispersants are mainly: aromatics, such as toluene, xylenes, polyalkylated benzenes and alkylnaphthalenes; chlorinated aromatics and chlorinated aliphatic hydrocarbons, such as chlorobenzenes, chloroethylenes and methylene chloride; (cyclo)aliphatic hydrocarbons, such as cyclohexane and paraffins, for example petroleum fractions; alcohols, such as butanol and glycol, and ethers and esters thereof; ketones, such as acetone, methyl ethyl ketone, methyl isobutyl ketone, isophorone and cyclohexanone; and strongly polar solvents and dispersants, such as dimethylformamide, N-methylpyrrolidone and dimethyl sulfoxide, solvents and dispersants of this type preferably having flash points of at least 30° C. and boiling points of at least 50° C., and water. Of the solvents and dispersants, so-called liquefied gaseous extenders or carriers are also suitable. These are products which are gaseous at room temperature and under atmospheric pressure. In the case where water is used as the solvent, it is possible, for example, also to use organic solvents as solvent aids.

The surfactants (wetting agents and emulsifiers) can be nonionic compounds, such as condensation products of fatty acids, fatty alcohols or fat-substituted phenols with ethylene oxide; fatty acid esters and ethers of sugars or polyhydric alcohols; products obtained from sugars or polyhydric alcohols by condensation with ethylene oxide; block polymers of ethylene oxide and propylene oxide; or alkyldimethylamine oxides.

The surfactants can also be anionic compounds, such as soaps; fatty sulfate esters, for example dodecyl sodium sulfate, octadecyl sodium sulfate and cetyl sodium sulfate; alkylsulfonates, arylsulfonates and fatty-aromatic sulfonates, such as alkylbenzenesulfonates, for example calcium dodecylbenzenesulfonate, and butyl-naphthalenesulfonates; and more complex fatty sulfonates, for example the amide condensation products of oleic acid and N-methyltaurine and sodium dioctyl sulfosuccinate.

Finally, the surfactants can be cationic compounds, such as alkyldimethylbenzylammonium chlorides, dialkyldimethylammonium chlorides, alkyltrimethylammonium chlorides and ethoxylated quaternary ammonium chlorides.

Suitable dispersants (without surfactant action) are mainly: sodium salts and ammonium salts of lignosulfonic acid, sodium salts of maleic anhydride/diisobutylene copolymers, sodium salts and ammonium salts of sulfonated polycondensation products of naphthalene with formaldehyde, sodium salts of polymeric carboxylic acids and sulfite waste liquors.

Examples of dispersants which can be used and are suitable in particular as thickeners or antisettling agents are methylcellulose, carboxymethylcellulose, hydroxyethylcellulose, polyvinyl alcohol, alginates, caseinates and blood albumin.

Examples of suitable stabilisers are acid-binding agents, for example epichlorohydrin., phenyl glycidyl ether and soya epoxides; antioxidants, for example gallic esters and butylhydroxytoluene; UV absorbers, for example substituted benzophenones, α-cyano-β,β-diphenylacrylic esters and cinnamic esters; and deactivators, for example salts of ethylenediaminetetraacetic acid and polyglycols.

Apart from the combinations according to the invention, the fungicidal compositions according to the invention can also contain other active substances, for example other fungicidal compositions [active substance components c) or d)]; insecticides and acaricides, bactericides, plant-growth regulators and fertilisers. These combination agents are suitable for widening the activity spectrum or for other favourable effects on the plant growth.

Depending on their type, the fungicides according to the invention in general contain between 0.0001 and 95 per cent by weight of the active substance combination according to the invention. In concentrates, the active substance concentration is usually in the upper region of the upper concentration interval. These forms can then be diluted with identical or different formulation agents to give active substance concentrations suitable for practical use, and these concentrations are usually in the lower region of the upper concentration interval. Emulsifiable concentrates in general contain 5 to 95 per cent by weight, preferably 25 to 85 per cent by weight, of the active substance combination according to the invention. Suitable application forms are, inter alia, ready-to-use solutions, emulsions and suspensions which are suitable, for example, as spray mixtures. In spray mixtures of this type, for example, concentrations between 0.0001 and 20 per cent by weight can be present. In the ultra-low volume process, it is possible to formulate spray mixtures in which the active substance concentration is preferably 0.5 to 20 per cent by weight, while the spray mixtures formulated in the low-volume process and the high-volume process preferably have an active substance concentration of 0.02 to 1.0 or 0.002 to 0.1 per cent by weight.

The fungicidal compositions according to the invention can be prepared by mixing an active ingredient combination according to the invention with formulation agents.

The compositions can be prepared in a known manner, for example by intimate mixing of the active substances with solid carriers, by dissolution or suspension in suitable solvents or dispersants, if appropriate with the use of surfactants as wetting agents or emulsifiers or of dispersants, by dilution of already prepared emulsifiable concentrates using solvents and dispersants, and the like.

In the case of pulverulent compositions, the active-substances can be mixed with a solid carrier, for example by joint grinding; or the solid carrier can be impregnated with a solution or suspension of the active substances and the solvent or dispersant can then be removed by slow evaporation, heating or by suction under reduced pressure. By adding surfactants or dispersants, pulverulent compositions of this type can be made easily water-wettable, enabling them to be converted into aqueous suspensions, which are suitable, for example, as sprays.

The active substance mixes according to the invention can also be mixed with a surfactant and a solid carrier in order to form a wettable powder, which is dispersible in water, or they can be mixed with a solid pregranulated carrier in order to form a granulated product If desired, the active substance mixtures according to the invention can be dissolved in a water-immiscible solvent, for example an alicyclic ketone, which advantageously contains a dissolved emulsifier, so that the solution has a self-emulsifying effect when added to water. Otherwise, the active substance combinations can be mixed with an emulsifier and the mixture can be then diluted with water to the desired concentration. Moreover, the active substance combinations can be dissolved in a solvent and then mixed with an emulsifier. Such a mixture can likewise be diluted with water to the desired concentration. This gives emulsifiable concentrates or ready-to-use emulsions.

The compositions according to the invention can be used by the application methods customary in plant protection or agriculture. The process according to the invention for controlling harmful fungi comprises treating the location of plant growth to be protected or the plant material to be protected, for example plants, pans of plants or plant propagation material (e.g. seed), with an active amount of an active substance combination according to the invention or a composition according to the invention.

FORMULATION EXAMPLES

Example 1

| Example 1: Emulsifiable concentrate (EC) | |
|---|---|
| Fenpropimorph | 375 g/L |
| RH-7592 | 50 g/L |
| N-Methylpyrrolidone (auxiliary solvent) | 100 g/L |
| Nonylphenol polyethoxylate (nonionic emulsifier) | 50 g/L |
| Calcium dodecylbenzenesulfonate (anionic emulsifier) | 25 g/L |
| Alkylbenzene mixture (solvent) | balance to 1000 ml |

Such a concentrate can be diluted with water to give application mixes for the treatment of leaves, the treatment of soil or the treatment of parts of plants.

Example 2

| Example 2: Emulsifiable concentrate (EC) | |
|---|---|
| Fenpropidin | 240 g/L |
| RH-7592 | 40 g/L |
| N-Methylpyrrolidone (auxiliary solvent) | 40 g/L |
| Isotridecanol polyethoxylate (nonionic emulsifier) | 50 g/L |
| Calcium dodecylbenzenesulfonate (anionic emulsifier) | 25 g/L |
| Isohexyl acetate (solvent) | balance to 1000 ml |

All components are dissolved with stirring, the dissolution process being accelerated by gentle heating.

Example 3

| Example 3: Emulsifiable concentrate (EC) | |
|---|---|
| Fenpropimorph | 50 g/L |
| Fenpropidin | 50 g/L |
| RH-7592 | 50 g/L |
| N-methylpyrrolidone (auxiliary solvent) | 50 g/L |
| Nonylphenol polyethoxylate (nonionic emulsifier) | 50 g/L |
| Calcium dodecylbenzenesulfonate (anionic emulsifier) | 25 g/L |
| Alkylnaphthalene mixture (solvent) | balance to 1000 ml |

All components are dissolved with stirring, the dissolution process being accelerated by gentle heating.

The resulting solutions are emulsified in water according to Example 1 to Example 3 and thus produce a ready-to-use spray mixture in a desired dilution. Such solutions are used for protecting plants or parts of plants (seeds, cuttings, tubers, and the like) against infection with fungi.

Example 4

| Example 4: Wettable powder (WP) | |
|---|---|
| Fenpropimorph | 25% w/w |
| RH-7592 | 25% w/w |
| Hydrated silica (silica carrier) | 25% w/w |
| Nonylphenol polyethoxylate (wetting agent) | 4% w/w |
| Sodium polycarboxylate (dispersant) | 4% w/w |
| Calcium carbonate (inert material, carrier) | 17% w/w |

To prepare this wettable powder, fenpropimorph and nonylphenol polyethoxylate are mixed in a first working procedure and sprayed onto the initially introduced silica in a powder mixer.

The further components are then admixed and milled, for example, in a pinned disc mill to a fine powder.

The resulting wettable powder, when stirred into water, gives a fine suspension in the desired dilution, which is suitable as ready-to-use spray mixture, for example for dressing plant propagation material, such as plant tubers, root material and leaf material of seedlings or of plant seeds.

Example 5

| Example 5: Wettable powder (WP) | |
| --- | --- |
| Fenpropimorph | 15% w/w |
| Fenpropidin | 25% w/w |
| RH-7592 | 10% w/w |
| Sodium lignosulfonate | 5% w/w |
| Sodium diisobutylnaphthalenesulfonate | 6% w/w |
| Octylphenol polyethylene glycol ether (7–8 mol of ethylene oxide) | 2% w/w |
| Highly disperse silica | 10% w/w |
| Kaolin | 27% w/w |

Example 6

| Example 6: Wettable powder (WP) | |
| --- | --- |
| Fenpropimorph | 50% w/w |
| Fenpropidin | 20% w/w |
| RH-7592 | 5% w/w |
| Sodium lauryl sulfate | 5% w/w |
| Sodium diisobutylnaphthalenesulfonate | 10% w/w |
| Highly disperse silica | 10% w/w |

The active ingredients from Examples 5 and 6 are thoroughly mixed with the additives and thoroughly ground in a suitable mill. This gives wettable powders which can be diluted with water to give suspensions of any desired dilution.

Example 7

| Example 7: Dusts | |
| --- | --- |
| Fenpropimorph | 6% w/w |
| RH-7592 | 2% w/w |
| Kaolin | 87% w/w |
| Highly disperse silica | 5% w/w |

Dusts ready for application are obtained by mixing the active substances with the carder and grinding the mixture in a suitable mill.

BIOLOGICAL EXAMPLES

Mycelium growth test using *Helminthosporium repentistrifici* a) Method:

The fungal strain is cultured at 18° C. and 16 hours/-day of simulated sunlight irradiation for 7 days on potato-dextrose-agar (PDA), which contains one or both active substances or is free of active substance (control). To this end, active substances I and II are each dissolved in pure ethanol and mixed in the desired relative amounts and diluted. A specified amount is then added to the liquid PDA medium at 50° C. and intimately mixed therewith. Agar media having active substance concentrations of 30; 10; 3; 1; 0.3; 0.1; 0.03 and 0.01 mg of a.i./liter are prepared. The ethanol concentration in the medium is uniformly 0.1%.

The liquid culture medium is then poured into Petri dishes (9 cm diameter) and inoculated in the centre using an agar disc (5 mm diameter), which was stamped out from a 7 day old fungal culture. The inoculated dishes are incubated at 18° C. in an air-conditioned chamber in the dark for 5 days. Each test is repeated 3 or 4 times.

b) Evaluation:

After the incubation period, the diameter of the colony is determined. The fungicidal actions according to Abbott are convened into C. I. Bliss, probit values (1935)* plotted against the logarithms of the fungicide concentrations to give a dose-action relationship. This probit-log graph converts the dose/action curve into a straight line (D. L. Finney 1971 "Probit analysis", 3rd edition, Cambridge, UK: Cambridge University Press). The linear regression and the ED-50 values (effective dosage) are determined from this straight line.

*Bliss, C. I. Ann. Appl. Biol. 22, 134-167 (1935)

c) Calculation of the synergistic factors (SF) of fungicides in a mixture

The theoretical effect ($ED_{th}$) of a mixture can be calculated using the formula of Wadley (**) if the ED values of the individual components of the mixture are known:

**Wadley, F. M. (1945) The evidence required to show synergistic action of insecticides and a short cut in analysis. ET-223, U.S. Department of Agriculture, 8 pp. Wadley, F. M. (1967) Experimental Statistics in Entomology Washington, U.S.A.: Graduate School Press, U.S.D.A.

$$ED\text{-}50(th) = \frac{a + b}{\frac{a}{ED\text{-}50_a} + \frac{b}{ED\text{-}50_b}}$$

$a$, $b$ = ratios of the fungicides in the mixture

The ratio of the calculated theoretical effect ($ED_{th}$) and the actually observed effect ($ED_{ob}$) of the mixture gives the synergic factor (SF).

$$SF = \frac{ED\text{-}50(th)}{ED\text{-}50(ob)}$$

| | |
|---|---|
| $SF > 1.2$ | synergistic interaction |
| $SF > 0.5 < 1.2$ | additive interaction |
| $SF < 0.5$ | antagonistic interaction |

According to V. Gisi et al. (1987) and Y. Levy et al. (1986), a synergistic interaction is already observed with SF values of greater than 1.0.(***)

***Gisi, U., Binder, H., Rimbach, E. (1985) Synergistic interactions of fungicides with different modes of action. Trans. Br. mycol. Soc. 85 (2), 299-306 Levy, Y. et al (1986) The joint action of fungicides in mixture: comparison of two methods of synergy calculation. Bulletin OEPP 16, 651-657 (1986)

The limits of the synergistic factor of a certain mixture are determined using the standard deviation of the ED values observed. SF values of greater than 1.2 give a statistically significant synergism.

d) Results using active substance I and active substance II

Activities of the individual components and of the mixture (ED-50)

TABLE 1

| Active substance | Test No. 1 | 2 | 3 |
|---|---|---|---|
| I | 2.7 | 3.5 | 2.2 |
| II | 2.3 | 1.7 | 0.9 |
| I:II = 1:1 | 1.6 | 1.5 | 0.6 |
| SF of the ED-50 values | 1.6 | 1.5 | 2.1 | e) Results using active substance I and active substance III

Activities of the individual components and of the mixture (ED-50)

TABLE 2

| Active substance | Test No. | | | |
| --- | --- | --- | --- | --- |
| | 1 | 2 | 3 | 4 |
| I | 2.7 | 3.5 | 2.9 | 2.2 |
| III | 2.5 | 1.8 | 1.4 | 2.2 |
| I:III = 1:1 | 1.9 | 1.7 | 0.9 | 0.7 |
| SF of the ED-50 values | 1.4 | 1.4 | 2.1 | 3.1 | f) Comment

The values from Tables 1 and 2 show for each of the three and four independently run tests that the fungicidal action of a mixture comprising active substance I and active substance II and of a mixture comprising active substance I and active substance III undergoes a significant increase, i.e. a synergistically increased action is present. As can be seen, these actions are each time reproducible.

Similar results are obtained with Alternaria brassicae, Helminthosporium oryzae, Rhizoctonia solani and Fusarium culmorum.

What is claimed is:

1. A fungicidal composition containing a synergistic fungicidally effective amount of at least two active ingredients, wherein one active ingredient is:
   a) 4-(4-chlorophenyl)-2-phenyl-2-[(1H-1,2,4-triazol-1-yl)methyl]butane nitrile, or an acid addition salt or metal complex thereof, and the second active ingredient is:
   b) fenpropidin or an acid addition salt thereof, together with a suitable carder, wherein the weight ratio of the active ingredients a) and b) is in the range of 2:1 to 1:20.
2. A composition of claim 1, wherein the weight ratio of the active ingredients a) and b) is 1:1 to 1:4.
3. A process for controlling fungi, comprising the step of treating plant material or its location, infected or liable to be infected with fungi, with a synergistic fungicidally effective amount of a composition of claim 1.
4. The process of claim 3, wherein the plant material is plant propagation material.

* * * * *